United States Patent [19]

Wolin et al.

[11] Patent Number: 5,459,253
[45] Date of Patent: Oct. 17, 1995

[54] M-RNA PURIFICATION

[75] Inventors: Christopher D. Wolin, Milwaukee; Phillip P. Franciskovich, Brown Deer, both of Wis.

[73] Assignee: Pharmacia P-L Biochemicals Inc., Milwaukee, Wis.

[21] Appl. No.: 237,965

[22] Filed: May 2, 1994

Related U.S. Application Data

[63] Continuation of Ser. No. 42,896, Apr. 5, 1993, abandoned, which is a continuation of Ser. No. 732,549, Jul. 19, 1991, abandoned.

[51] Int. Cl.$^6$ .............................. C12N 15/10; C12Q 1/68; C07H 1/08; C07H 21/02
[52] U.S. Cl. .................. 536/25.42; 536/25.4; 536/25.41; 435/6; 435/172.3; 435/810; 935/4; 935/21
[58] Field of Search ................................ 536/25.4, 25.41, 536/25.42; 935/4, 21; 435/172.3, 6, 810

[56] References Cited

FOREIGN PATENT DOCUMENTS 0127327  12/1984  European Pat. Off. .
WO8706621  11/1987  WIPO .

OTHER PUBLICATIONS

Pharmacia "RNA Extraction Kit Instruction Booklet" (1989).
Pharmacia "M-RNA Purification Kit Instruction Booklet" (1989).
H. Aviv et al., 69 P.N.A.S. USA 1408–1412 (1972).
C. Wolin et al, 16 Analects 1–4 (1988).
C. Wolin et al., 17 Analects 1, 5–7 (1989).
K. Jakobsen et al., 18 Nuc. Acids Res. 3669 (Jun. 25, 1990).
J. Bradley et al., 6 BioTechniques 114–116 (1988).
J. Chirgwin et al., 18 Biochemistry 5294–5299 (1979).
P. Chomczynski et al., 162 Anal. Biochem. 156–159 (1987).
P. Chomczynski et al., Cinna/Biotecx Bulletin #1 (1988).
Pharmacia LKB New Product Announcement, admitted prior art "RNA Extraction Kit" (1989).
J. Thompson et al., Analytical Biochemistry 181:371–378 (1989).
J. Thompson et al. "A Noise–Free Molecular Hybridization Procedure for Measuring RNA in Cell Lipates" Anal. Biochem. 181:371–378 (1989).
Pellegrino, M. G. et al., "A Sensitive Solution Hybridization . . ." Biotechniques 5(5) 452–458 (1987).

*Primary Examiner*—Keith C. Furman
*Assistant Examiner*—Rebecca Prouty
*Attorney, Agent, or Firm*—Quarles & Brady

[57] ABSTRACT

A method kit for purification of m-RNA from a cell are disclosed. Guanidine containing moieties, at high molarity, are use to quickly lyse the cell. They also act to inhibit RNase activity. Without the need for isolation of total RNA, the lysate can then be directly purified from the lysate using oligo dT (or U) by reducing the guanidine concentration via a dilution step.

2 Claims, 3 Drawing Sheets

$$A = \begin{array}{l} HN=C=S \\ H_2CO_3 \\ HCl \\ HNO_3 \\ H_2SO_4 \\ H-S-C\equiv N \end{array}$$

M-RNA PURIFICATION

This application is a continuation of application Ser. No. 08/042,896, filed Apr. 5, 1993, which is in turn a continuation of application Ser. No. 07/732,549, filed Jul. 19, 1991, both now abandoned.

FIELD OF THE INVENTION

This invention relates to a way to purify messenger RNA ("m-RNA") from cells. More particularly, it relates to oligo dT chromatography techniques that can be used with a crude cell lysate containing a guanidine salt.

BACKGROUND OF THE INVENTION

Isolation of intact m-RNA is required for many biological procedures. For example, m-RNA can be used for cDNA synthesis, in vitro translation, and/or "Northern" hybridization. See e.g. J. Sambrook et al., *Molecular Cloning: A Laboratory Manual* (Cold Spring Harbor 1989). The disclosures of this publication and the disclosures of all other publications recited herein are incorporated by reference as if fully set forth herein.

Messenger RNA is a particularly difficult macromolecule to isolate from cells. This is due to the presence of RNase in cells which will rapidly degrade the RNA upon disruption of the cellular compartments. Therefore, cells in which RNA is to be isolated have been disrupted in the presence of a number of different denaturants (i.e. phenol, LiCl, SDS) and RNase inhibitors (i.e. heparin, iodoacetate, diethyl pyrocarbonate, polyvinyl sulfate, aurin tricarboxylic acid).

The best denaturant/inhibitors known are guanidine salts (e.g. guanidine isothiocyanate a/k/a guanidinium thiocyanate). They are used to isolate an intermediate product, total RNA. See P. Chomczynski et al., 162 Anal Biochem. 156–159 (1987); J. Chirgwin et al., 18 Biochemistry 294–5299 (1979). After cell lysis using the guanidine salt, cellular matter is subjected to extended equilibrium centrifugation in CsCl or CsTFA during which total RNA becomes pelleted at the bottom of the tube.

Following aspiration of the supernatant, the total RNA pellet is redissolved in a buffer. This separates total RNA from guanidine salts (and unfortunately thus removes RNase inhibitors). Once total cellular RNA has been isolated, the mRNA can then be purified by the passage of total RNA over a column of oligo d(T)-cellulose. H. Aviv, et al., 69 P.N.A.S. USA 1408–1412 (1972). This method capitalizes on the presence of long stretches of adenyl residues at the 3' end eukaryotic m-RNA. Under suitable conditions of high salt, hydrogen bonding between the adenylated mRNA and the oligo d(T) will form, and the mRNA will be retained on the column. The mRNA is subsequently eluted in the presence of a no-salt buffer.

The above method of mRNA isolation has been improved by purification of mRNA from total RNA on a column (which is oligo d(T) bound to a solid support) in spun column format. Such columns are available from Pharmacia, or from Clonetech, or 5'–3'. However, this method of total RNA isolation followed by mRNA purification can still take many hours (or sometimes days) to complete.

Attempts have been made to reduce the time needed for m-RNA isolation. See K. Jakobsen et al., 18 Nuc. Acids Res. 3669 (Jun. 25, 1990); J. Badley, 6 BioTechniques 114–116 (1988). However, these approaches did not involve guanidine moieties. Instead they relied upon proteases or LiCl to disrupt the cell, neither of which gave adequate RNase protection. Further, the protease system had other problems (e.g. inadequate lysing capability).

Thus, a need still exists for an improved mRNA isolation technique.

SUMMARY OF THE INVENTION

In one aspect, the invention provides a method for separating m-RNA from a eukaryotic cell (e.g. fatty acids, other proteins, significant quantities of other RNA besides m-RNA). One exposes the cell to a guanidine containing moiety so as to lyse the cell. Without the need to separate out total RNA, one then exposes the lysate to oligo d(T) or oligo U under conditions where the molarity of guanidine is less than 3M and at least a portion of the m-RNA will bind to the oligo.

Preferably, the oligo dT or U is bound to a fixed support (e.g. cellulose), and the last step in the method involves elution of the m-RNA bound to the support from the column in the presence of a no-salt buffer. In another preferred form, the lysis step occurs in at least 3.5 molar guanidine. Thereafter, the molarity of guanidine is reduced by a dilution step to below 2.5M (preferably to 1.5M) prior to the column purification.

In another aspect, the invention provides a kit comprising an oligo dT or U support and a guanidine containing compound.

It has surprisingly been discovered that even though guanidine salts are usually highly disruptive of binding, and therefore strongly interfere with m-RNA binding to an oligo dT support, there is a small molarity range where the guanidine will still serve to inhibit RNase yet not significantly disrupting oligo dT binding. Thus, if standard guanidine lysis conditions (4M–5M guanidine) are used, one dilutes the lysate after lysis. As a result, one can then directly (and without a centrifugation or isolation step to obtain total RNA) use an oligo dT column to isolate m-RNA directly. The overall process can usually be completed in under an hour.

An object of the present invention is therefore to provide a method of the above kind that significantly reduces the time needed for m-RNA isolation, while not subjecting the m-RNA to unnecessary RNase degradation.

Another object is to provide a kit for performing such methods.

Yet another object is to enable isolation of m-RNA from extremely small samples of starting material (e.g. a single cell).

The foregoing and other objects and advantages of the invention will appear from the following description. In the description reference is made to preferred embodiments of the invention. Such embodiments do not necessarily represent the full scope of the invention. Thus, reference should be made to the claims for interpreting the full scope of the invention.

DESCRIPTION OF THE PREFERRED EMBODIMENTS

Materials

All reagents were prepared in water pretreated with diethyl pyrocarbonate ("DEPC") as an extra precaution to insure inactivation of any contaminating RNase molecules. A 0.1% solution of DEPC in distilled water was allowed to stand overnight at room temperature, then autoclaved.

The "Extraction Buffer" contains the following reagents in order at addition: 100 mm potassium phosphate, pH7.0; 10 mm EDTA; 4.5M GTC; and 1% sodium lauryl sarcosine.

The oligo(dT)-cellulose spun columns are Pharmacia Type 7 oligo(dT)-cellulose suspended in a storage buffer containing 0.15% Kathon CG®.

The "High-Salt Buffer" is 10 mMTris-HCl (pH 7.4), 1 mM EDTA, 0.5M NaCl.

The "Low-Salt Buffer" is 10 mM Tris-HCl (pH 7.4), 1 mM EDTA, 0.1M NaCl.

The "Elution Buffer" is 10 mM Tris-HCl (pH 7.4), 1 mM EDTA.

The "Glycogen Solution" is 10 mg/ml glycogen in DEPC-treated water.

The "K Acetate Solution" is 2.5M potassium acetate (pH 5.0).

The procedure described below was initially tested using calf liver as the cell source. It was subsequently shown that a number of tissues and other sources can be used in the procedure (e.g. HeLa cells, Drosophila melanogaster, Saccharomyces cerevisiae, Tetrahymenia, murine kidney, Zea mays, and Arabadopsis thaliana).

Overview

Figure 3:
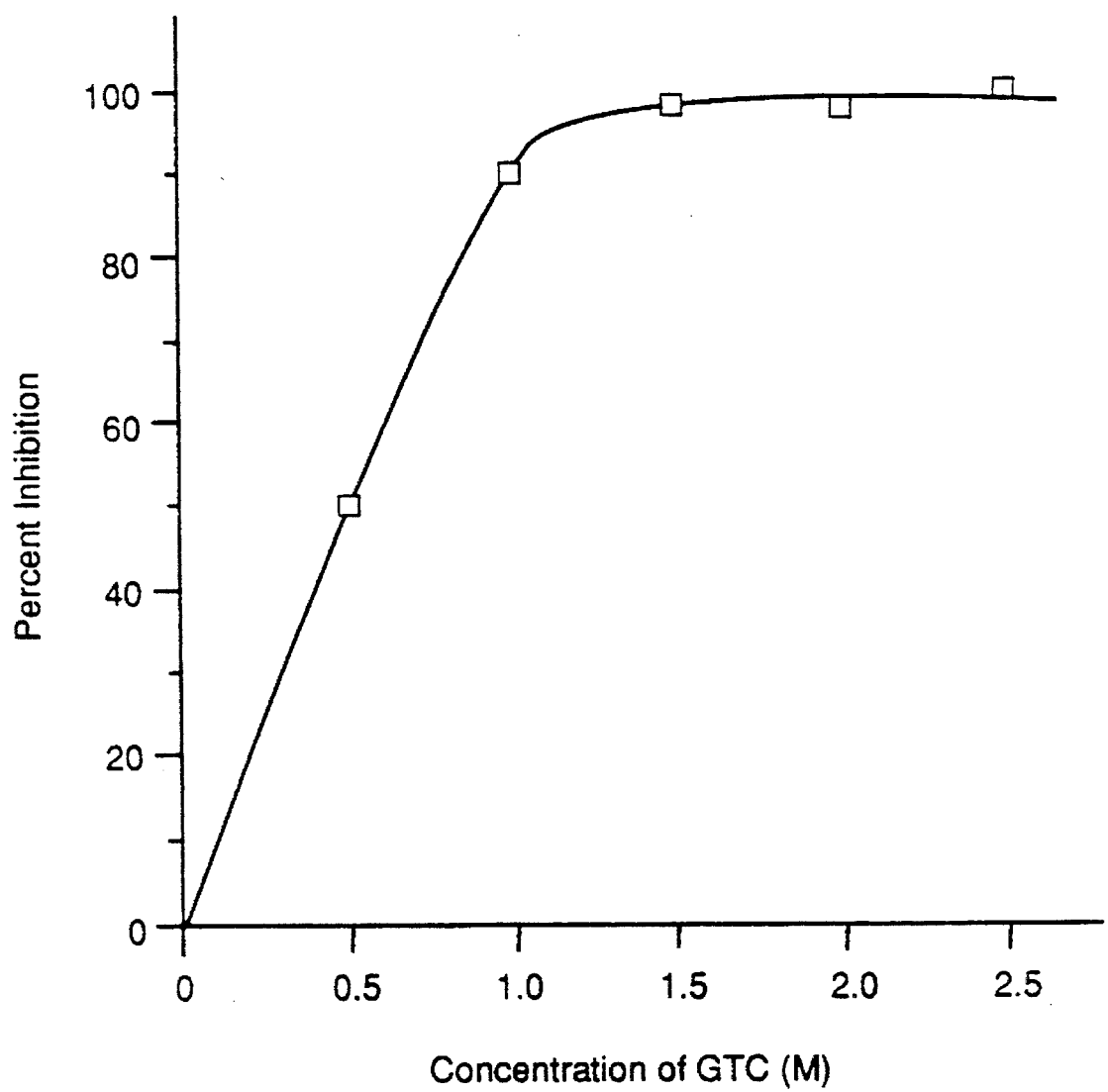
FIG. 3 is a chart showing how RNase inhibition is affected by GTC concentration.

The biological material is extracted by homogenization in 1.5 ml "Extraction Buffer" which is 4.5M guanidinium isothiocyanate condition. This high GTC level ensures the rapid inactivation of endogenous RNase activity and substantially complete dissociation of cellular components from the m-RNA (see FIG. 3).

Figure 2:
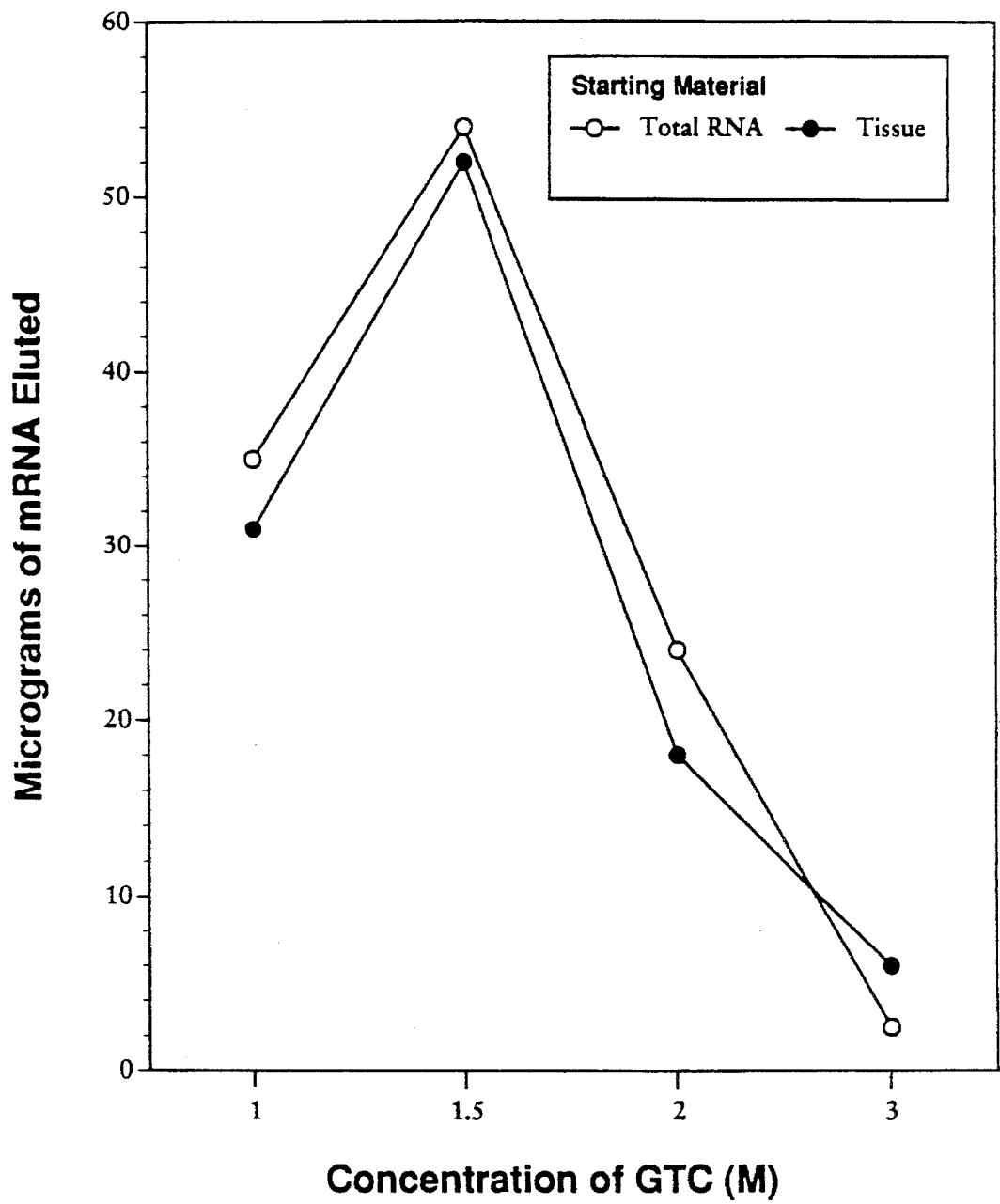
FIG. 2 is a chart showing how oligo dT binding to m-RNA is affected by guanidine isothiocyanate ("GTC") concentration. This figure was generated by taking 1 mg aliquots of calf liver total RNA, or 0.25 mg calf liver tissue were homogenized in various concentrations of guanidine isothiocyanate. The samples were applied to oligo (dT)-cellulose.

The extract is then diluted with 3ml no-salt buffer ("Elution Buffer"), to reduce the GTC concentration to 1.5M. The RNA is still protected from RNase contamination under this condition (see FIG. 3). The concentration of GTC is now optimal for efficient hydrogen bonding between poly (A) tracts on m-RNA molecules and oligo (dT) attached to a support (FIG. 2). As an added benefit, the dilution causes a number of proteins to precipitate, allowing a primary purification.

After a brief second homogenization, the extract is clarified by a brief centrifugation, the supernatant is poured into an oligo (dT)-cellulose spin column, and the polyadenylated fraction is allowed to bind over a 10 minute period. The column is subjected to a low-speed centrifugation, and the liquid containing non-bound material is decanted. The matrix is batch-washed sequentially in 3 ml units with High-Salt and Low-Salt buffer and the m-RNA is eluted with 3 aliquots of 0.25 ml prewarmed Elution Buffer. Further details are given in the procedures below.

Procedure A1—Tissue Sample

Approximately 20–30 minutes before the tissue or cell sample will be ready for extraction, remove the Extraction Buffer from storage at 4° C. and place it at 37° C. Shake the container occasionally, until all the crystalline material is dissolved. Cool to room temperature.

Place up to 0.5 g tissue in a chilled homogenizer (either manual or mechanical) and add 1.5 ml of Extraction Buffer. Homogenize the tissue until it is a uniform suspension. Avoid the generation of excess heat or foam.

To dilute the sample, add 3 ml of Elution Buffer to the extract and mix thoroughly. Homogenize briefly, then transfer the homogenate into a sterile polypropylene centrifuge tube. Place the remaining Elution Buffer at 65° C. until needed.

After assuring that each tube is counter-balanced, centrifuge the diluted extract at approximately 12,000×g (e.g. 10,000 rpm in a Beckman JA 20 rotor) for 5–10 minutes at room temperature. Then proceed to Procedure B.

Procedure A—Cultured Cells

To extract cells grown as a monolayer, drain the culture medium from the cells in one 75 $cm^2$ flask, then add 1.5 ml of Extraction Buffer directly onto the cells. Swirl the buffer over the monolayer to assure complete cell lysis. If desired, this suspension can be transferred onto an additional monolayer to lyse these cells.

Alternately, first treat the cells with trypsin before extraction. This should be the method chosen to pool cells from several plates or flasks. Using standard procedures, treat the cells with trypsin to detach them, centrifuge to pellet them, and resuspend them in phosphate-buffered saline or similar solution. Pellet the cells by centrifugation, and discard the supernatant. Add 1.5 ml of Extraction Buffer.

To extract cells grown in suspension, pellet the cells by centrifugation, and decant and discard the supernatant. Then add 1.5 ml of Extraction Buffer to the pelleted cells.

To assure a homogeneous extract, disrupt the cells using a homogenizer or pass the extract through a 21-gauge needle attached to a syringe. To dilute the sample, add 3 ml of Elution Buffer to the extract and mix thoroughly. Homogenize briefly, then transfer the homogenate into a sterile polypropylene centrifuge tube. Place the remaining Elution Buffer at 65° C. until needed.

After assuring that each tube is counter-balanced, centrifuge the diluted extract at approximately 12,000×g (e.g. 10,000 rpm in a Beckman JA 20 rotor) for 5–10 minutes at room temperature. Then proceed to Procedure B.

Procedure B—Isolation of m-RNA

Invert an Oligo(dT)-Cellulose Spun Column (preferably Pharmacia column 27-9254-01) several times to resuspend the matrix. Remove both top and bottom closures, place the column in a 15 ml centrifuge tube and balance against a counterweight. Centrifuge at 350×g for 2 min.

Remove the column from the centrifuge tube and discard the liquid in the tube. Replace the bottom closure on the drained column and place it upright in a rack.

Using a sterile pipette, transfer 4 ml of the supernatant from the final step in Procedure A onto the surface of the resin of the Oligo(dT)-Cellulose Spun Column. Avoid disturbing the pelleted cellular material during this transfer. Replace the top closure of the column, and invert the column several times to resuspend the resin. Gently mix for 10 minutes by inverting the column manually or by placing it on a rocking table or similar device.

Leaving both top and bottom closures securely on, place the column in a 15 ml centrifuge tube and balance against a counterweight. Centrifuge at 350×g for 2 minutes to separate the resin from the suspension. Remove the top closure, decant the supernatant and discard it. Avoid disturbing the resin.

Apply 3 ml of High-Salt Buffer to the top of the resin and replace the top closure of the column. Resuspend the matrix by gentle mixing. This may require one to tap the bottom of the column several times. Place the column in a 15 ml tube and balance against a counterweight. Centrifuge at 350×g for 2 minutes. Remove the top closure, decant the supernatant and discard it. Repeat the wash using High-Salt Buffer two more times, exactly as described in the step above.

Apply 3 ml of Low-Salt Buffer to the column and replace the top closure. Resuspend the matrix by gentle mixing. This may require tapping the bottom of the column several times. Place the column in a 15 ml centrifuge tube and balance against a counterweight. Centrifuge at 350×g for 2 minutes. Remove the top closure, decant the supernatant and discard it.

Remove the bottom closure. Apply 3 ml of Low-Salt Buffer to the top of the resin. Balance against a counterweight. Centrifuge at 350×g for 2 minutes. Place a sterile 1.5 ml screw-top microcentrifuge tube inside a 15 ml centrifuge tube. Place the column inside the 15 ml centrifuge tube in such a way that the tip of the column is inside the opening of the screw-top microcentrifuge tube (the "collection tube").

Elute the bound poly(A)$^+$ RNA using three successive washes with Elution Buffer prewarmed to 65° C. For each wash, pipette 0.25 ml of buffer onto the top of the column; balance the column (in its collection tube) against a counterweight; then centrifuge at 350×g for 2 minutes. Do not change the collection tube between washes, so that the entire 0.75 ml elute is collected in the same sterile tube.

Remove the screw-top microcentrifuge tube from the 15 ml centrifuge tube using clean (flamed) forceps. Place the collected sample and remaining Elution Buffer on ice.

Precipitation

While precipitation is not always needed, for some uses it may be desirable. To precipitate the isolated mRNA, add 50 μl of K Acetate Solution and 10 μl of Glycogen Solution to 0.5 ml of sample. Add 1 ml of 95% ethanol (chilled to −20° C.) and place the sample at −20° C. for a minimum of 30 minutes. If the volume of the RNA to be precipitated is more that 0.5 ml, there is a need to transfer the material to a larger tube and add proportionally more K Acetate Solution (1/10 volume) and ethanol (2–2½ volumes). The amount of Glycogen Solution should remain constant, regardless of volume.

Collect the precipitated mRNA by centrifugation in a micro-centrifuge at 4° C. for 5 minutes. If the RNA is not to be used immediately, store it in this precipitated state (in ethanol) at −80° C. Decant the supernatant and invert the tube over a clean paper towel. Gently tap the tube on the towel to facilitate the removal of excess liquid. Redissolve the precipitated RNA in an appropriate volume of Elution Buffer or DEPC-treated water.

General Considerations

An important consideration in the purification of RNA is protection of the sample from contamination with RNases. Thus, any plastic or glassware which may come into contact with the sample should preferably be autoclaved or otherwise treated to prevent RNase contamination. Fresh gloves should be worn during the purification, both to protect the researcher from contact with solutions and to protect the RNA from nucleases present on the skin.

A centrifuge with a swinging-bucket rotor capable of accommodating a 15 ml centrifuge tube with a spun column inserted into it is preferred. For consistent results, it is important to maintain the correct time and speed of centrifugation. The buckets, column and counterweight should be balanced prior to centrifugation. This is especially important during sample elution.

Procedures A and B should be performed without pause, from disruption of cells or tissue to elution of the poly(A)$^+$ RNA. Thus all materials should be ready before starting Procedure A. The Extraction Buffer should be warmed to room temperature, with any crystallized material completely dissolved, before use. Work should be at room temperature except where specifically directed otherwise.

Figure 1:
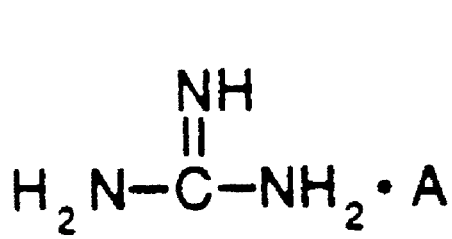
FIG. 1 depicts various guanidine salts. The list of potential hydrogen donors ("A") is by way of example.

It will be appreciated that the present invention dramatically reduces the time required to isolate m-RNA while protecting the m-RNA from RNase. Many modifications and variations of the preferred embodiments are possible without deviating from the spirit and scope of the invention. For example, some compounds that have a "guanidine containing moiety" are:

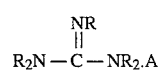

where A is a hydrogen or cation donator (e.g. see FIG. 1) and R is either H or lower alkyl.

Oligo U supports should also work. Further, the format of exposure needed not be a column. Compare K. Jakobsen, et al., 18 Nuc. Acids Res. 3669 (1990) where magnetic microspheres bound to oligo dT were described. Further, a wide variety of eukaryotic tissue and culture cells are possible. Thus, applicants' invention is not to be limited to just the examples shown.

We claim:

1. A method for preparative separation of mRNA from a eukaryotic cell, wherein the mRNA has a eukaryotic poly(A) tail, comprising:

exposing the cell to a solution containing at least 3.5 molar guanidine salt so as to lyse the cell, wherein a lysate is formed;

diluting the lysate so that concentration of guanidine salt is decreased;

then exposing the diluted lysate to oligo dT or oligo U under conditions where the molarity of the salt is greater than 0.05 molar and less than 3 molar so that the mRNA binds to oligo dT or oligo U, wherein the exposing step is at room temperature, and wherein during the exposing step the amount of mRNA bound to the oligo dT or oligo U essentially reaches its maximum level within ten minutes of exposure;

mixing the mRNA and oligo dT or oligo U during the exposing step; and then separating mRNA from oligo dT or oligo U.

2. A kit for separating m-RNA from a cell by the method of claim 1, comprising:

a support to which oligo T or oligo U is bound;

a compound having a guanidine-containing moiety; and instructions for practicing the method of claim 1.

* * * * *